(12) United States Patent
Lee et al.

(10) Patent No.: US 8,247,949 B2
(45) Date of Patent: Aug. 21, 2012

(54) SURFACE ACOUSTIC WAVE SENSOR DEVICE AND METHOD OF CONTROLLING LIQUID USING THE SAME

(75) Inventors: Hun Joo Lee, Seoul (KR); Soo Suk Lee, Suwon-si (KR); Eun Chul Cho, Seoul (KR)

(73) Assignee: Samsung Electronics Co., Ltd., Samsung-ro, Yeongtong-gu, Suwon-si, Gyeonggi-do (KR)

( * ) Notice: Subject to any disclaimer, the term of this patent is extended or adjusted under 35 U.S.C. 154(b) by 478 days.

(21) Appl. No.: 12/568,724

(22) Filed: Sep. 29, 2009

(65) Prior Publication Data
US 2010/0319439 A1  Dec. 23, 2010

(30) Foreign Application Priority Data
Jun. 18, 2009 (KR) ........................ 10-2009-0054394

(51) Int. Cl.
*H03H 9/25* (2006.01)
*G01N 29/02* (2006.01)

(52) U.S. Cl. ..................... 310/338; 310/313 R; 73/24.01
(58) Field of Classification Search ............. 310/313 R, 310/338; 73/24.01–24.06
See application file for complete search history.

(56) References Cited

U.S. PATENT DOCUMENTS

| | | | |
|---|---|---|---|
| 5,918,258 A * | 6/1999 | Bowers | 73/24.06 |
| 6,122,954 A * | 9/2000 | Bowers | 73/24.06 |
| 6,363,773 B1 * | 4/2002 | Bowers | 73/24.06 |
| 7,229,821 B1 * | 6/2007 | Edmonson et al. | 435/287.1 |

FOREIGN PATENT DOCUMENTS
KR   10-2008-0090645 A   10/2008

* cited by examiner

*Primary Examiner* — Thomas Dougherty

(57) ABSTRACT

A surface acoustic wave sensor device includes a main body and a liquid controller disposed external to the main body. The main body includes a sample chamber, a surface acoustic wave sensor connected to the sample chamber, a first disposal chamber connected to the surface acoustic wave sensor and channels connecting the sample chamber, the surface acoustic wave sensor and the first disposal chamber. The liquid controller controls flow of a sample through the main body.

20 Claims, 3 Drawing Sheets

SURFACE ACOUSTIC WAVE SENSOR DEVICE AND METHOD OF CONTROLLING LIQUID USING THE SAME

CROSS-REFERENCE TO RELATED APPLICATION

This application claims priority to Korean Patent Application No. 2009-54394, filed on Jun. 18, 2009, and all the benefits accruing therefrom under 35 U.S.C. §119, the content of which in its entirety is herein is incorporated by reference.

BACKGROUND

1) Field

The general inventive concept relates to a surface acoustic wave ("SAW") sensor and, more particularly, to a device including the SAW sensor and a method of controlling a liquid using the same.

2) Description of the Related Art

A surface acoustic wave sensor is a device that senses, e.g., detects, a target material, such as an analyte, using a surface acoustic wave ("SAW").

Generally, the SAW sensor is disposed on a substrate made of a piezoelectric material, and includes a receptor that binds to a specific desired target material on a surface of the SAW sensor. More specifically, when a solution containing the target material flows into the SAW sensor, signals, such as wavelengths, for example, are changed by mechanical, chemical and/or electrical reactions of the target material with the receptor. As a result, properties and/or characteristics of the target material may be determined by monitoring the changes in the signals.

A SAW sensor device is typically used to analyze and monitor a target material contained in a sample, such as a chemical liquid sample or a biological liquid sample (such as a body fluid, for example).

The SAW sensor is particularly sensitive to a pressure of a liquid, as well as to viscosity or density of a medium (such as the liquid), and corresponding mass changes on a surface of the SAW sensor. Accordingly, precise control of the liquid is desired to minimize noise, which is a signal change due to factors other than the detected mass changes, for example.

There is typically an abundant amount of target materials in a given target sample solution analyzed by the SAW sensor, and the abundant target materials cause contamination of valves and pumps, as well as channels and chambers, for example, in the SAW sensor device, as the liquid flows through the SAW sensor. As a result of the contamination, substantial errors are introduced when the target sample solution is analyzed.

To reduce and/or effectively prevent these and other errors, disposable, i.e., not reusable, valves and pumps are used. However, using disposable valves and pumps has disadvantages, which include reducing commercial and economic feasibility and efficiency of the SAW sensor.

SUMMARY

Exemplary embodiments include a surface acoustic wave ("SAW") sensor device which provides advantages that include, but are not limited to, substantially increased reliability and accuracy of analyses performed by the SAW sensor by effectively minimizing generation of noise while detecting and/or sensing predetermined materials in a liquid sample and performing quantitative analyses thereof, and a method of controlling a liquid using the same. Exemplary embodiments further provide a SAW sensor device having substantially improved economic and commercial feasibility and efficiency.

Alternative exemplary embodiments provide a method for moving and controlling a liquid by air pressure or ventilation from outside a SAW sensor device.

In an exemplary embodiment, a SAW sensor device includes a main body and a liquid controller disposed external to the main body. The main body includes a sample chamber, a SAW sensor connected to the sample chamber, a first disposal chamber connected to the SAW sensor, and channels connecting the sample chamber, the SAW sensor and the first disposal chamber. The liquid controller controls flow of a sample through the main body.

According to an alternative exemplary embodiment, a SAW sensor system includes a first SAW sensor device and a second SAW sensor device. Each of the first SAW sensor device and the second SAW sensor device includes a main body and a liquid controller disposed external to the main body. The liquid controller controls flow of a sample through the main body. The main body includes a sample chamber, a SAW sensor connected to the sample chamber, a first disposal chamber connected to the SAW sensor, and channels connecting the sample chamber, the SAW sensor and the first disposal chamber. A receptor is disposed on a surface of the SAW sensor of the first surface acoustic wave sensor device, but a receptor is not disposed on a surface of the SAW sensor of the second surface acoustic wave sensor device.

According to yet another exemplary embodiment, a method of controlling a liquid in a SAW sensor device is provided. The SAW sensor device includes a main body and a liquid controller disposed external to the main body. The main body includes a sample chamber, a SAW sensor connected to the sample chamber, a first disposal chamber connected to the SAW sensor, and channels connecting the sample chamber, the SAW sensor and the first disposal chamber. The method includes providing a driving force from the liquid controller, disposed external to the main body, to the main body, and moving the liquid from the sample chamber to the SAW sensor using the driving force.

According to still another exemplary embodiment, a device for controlling a liquid includes a SAW sensor. The SAW sensor includes a main body and a liquid controller disposed external to the main body. The liquid controller controls flow of a sample through the main body. The main body includes: a first sample chamber; a second sample chamber connected to the first chamber; a SAW sensor connected to the first sample chamber and the second sample chamber; a first disposal chamber connected to the SAW sensor; and channels connecting the first sample chamber, the second sample chamber, the SAW sensor and the first disposal chamber.

BRIEF DESCRIPTION OF THE DRAWINGS

The above and other aspects, features and advantages will become more readily apparent by describing exemplary embodiments in further detail with reference to the accompanying drawings, in which.

DETAILED DESCRIPTION

Figure 1:
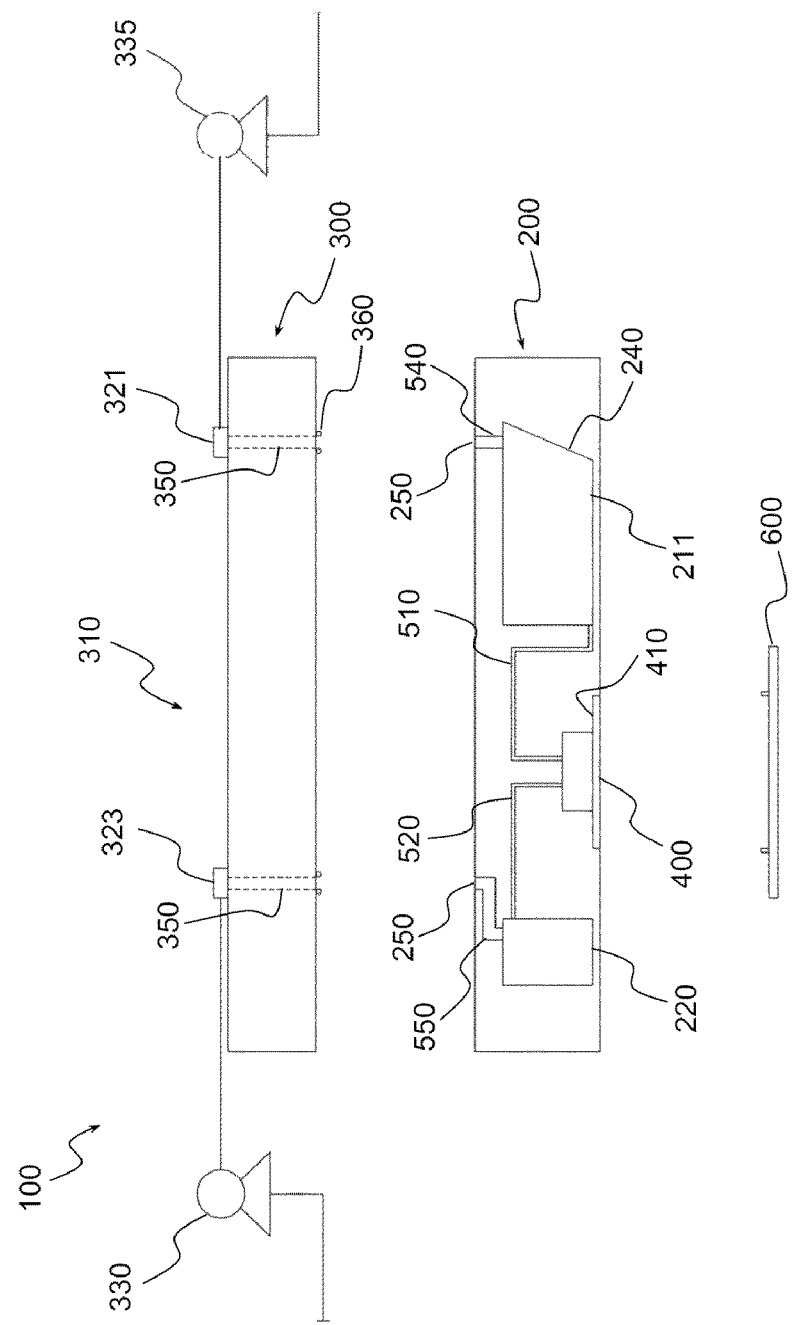
FIG. 1 is an exploded partial cross-sectional view of a an exemplary embodiment of a surface acoustic wave ("SAW") sensor device.

The invention now will be described more fully hereinafter with reference to the accompanying drawings, in which various embodiments are shown. This invention may, however, be embodied in many different forms, and should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

As will now be described in further detail with reference to the accompanying drawings, a surface acoustic wave ("SAW") sensor device according to an exemplary embodiment includes a main body including a sample chamber, a SAW sensor connected to the sample chamber, a disposal chamber connected to the SAW sensor, and which includes a sample passing through the SAW sensor, and channels connecting the sample chamber, the SAW sensor and the disposal chamber. In addition, the SAW sensor device according to an exemplary embodiment includes a liquid controller, which controls flow of a liquid, is disposed outside, e.g., external to, the main body.

In contrast with the exemplary embodiments described herein, a conventional SAW sensor device includes a liquid controller installed inside, e.g., internal to, a main body thereof, in a path or channel between a chamber and a SAW sensor, resulting in contamination of the liquid controller by a liquid sample therein, which causes generation of a substantial amount of noise.

However, according to exemplary embodiments described herein, the liquid controller is disposed outside the main body, and thus is not in direct contact with the chamber or the SAW sensor. Accordingly, contamination of the liquid controller and generation of noise is substantially reduced and/or is effectively prevented.

More particularly, the liquid controller in an exemplary embodiment may be disposed on an upper surface of the main body, e.g., a top surface of the main body, as will be described in further detail below. As a result, a liquid, e.g., a sample, is controlled from an upper portion of the sample chamber, and thus contact of the liquid with the liquid controller is effectively eliminated without application of external power, as will also be described in further detail below.

Figure 2:
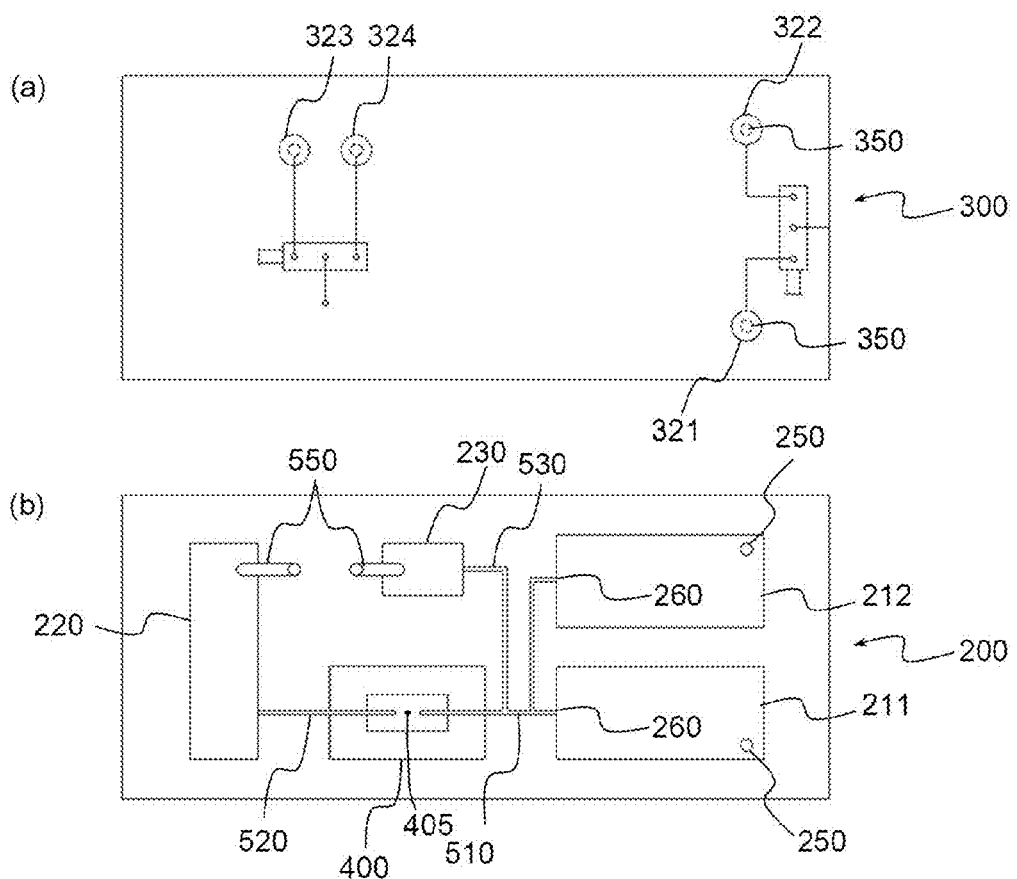
FIG. 2(a) is a plan view of a cover of the SAW sensor device of FIG. 1.
FIG. 2(b) is a plan view of a main body of the SAW sensor device of FIG. 1.
Figure 3:
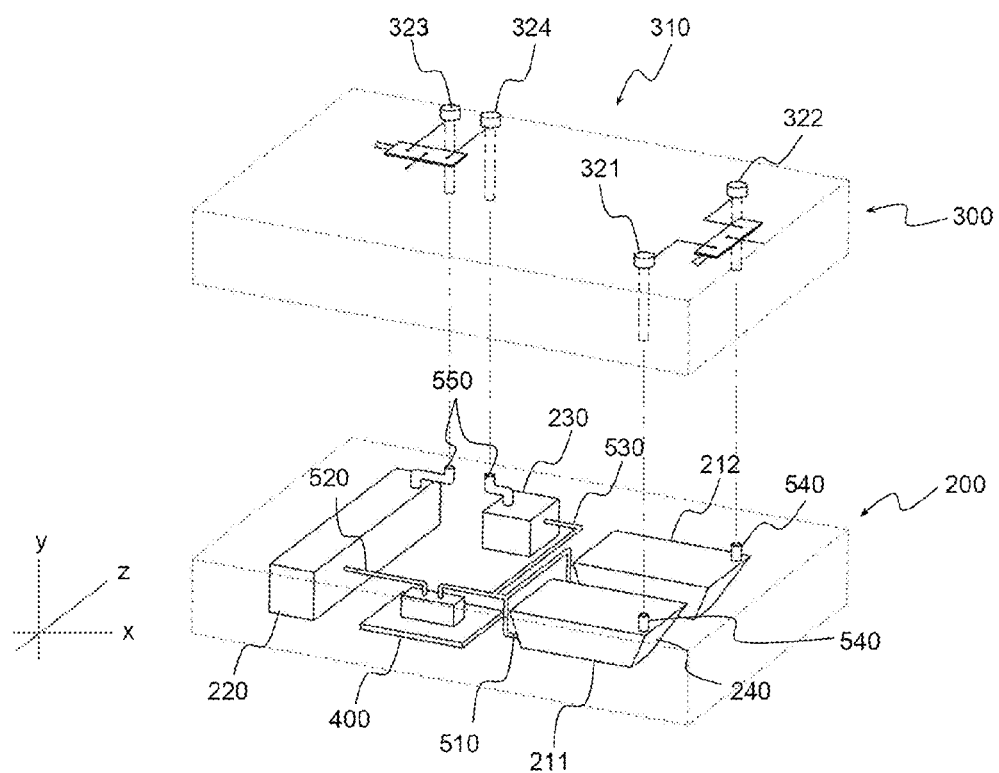
FIG. 3 is an exploded perspective view of the SAW sensor device of FIG. 1.

FIG. 1 is an exploded partial cross-sectional view of an exemplary embodiment of a SAW sensor device, FIG. 2(a) is a plan view of a cover thereof, FIG. 2(b) is a plan view of a main body thereof and FIG. 3 is an exploded perspective view thereof.

Referring to FIGS. 1-3, a SAW sensor device 100 according to an exemplary embodiment includes a main body 200, a cover 300 which covers an upper portion of the main body 200 and a liquid controller 310 disposed on the cover 300. The cover may be disposed on an upper surface, e.g., a top surface (as viewed in FIG. 1), of the main body 200. In an exemplary embodiment, the main body 200 includes a first sample chamber 211 and a second sample chamber 212, each containing a sample, such as a liquid, a SAW sensor 400 connected to the first sample chamber 211 and the second sample chamber 212 through a first channel 510, connected to both the first sample chamber 211 and the second sample chamber 212, and a first disposal chamber 220 connected to the SAW sensor 400 through a second channel 520.

The liquid controller 310 controls inflow/outflow of a sample, e.g., a liquid, within the main body 200 and, more particularly, through the SAW sensor 400. Specifically, the liquid controller 310 controls, among other things, a flow rate of the liquid through the main body 200, as will be described in greater detail below. In an exemplary embodiment, for example, the liquid controller 310 controls the flow of the liquid by adjusting an inflow and/or an outflow of air through the main body 200. To control the flow, exemplary embodiments of the liquid controller 310 include, but are not limited to, valves 321, 322, 323 and 324, which control the inflow/outflow of the liquid, as well as one or more pumps (e.g., a negative pressure pump 330 and/or a positive pressure pump 335), which control the flow pressure and/or flow rate of the liquid through the main body 200 and, subsequently, through the SAW sensor 400.

More specifically, the valves 321, 322, 323 and 324 control whether a sample solution is inputted to a surface of the SAW sensor 400 during operation of the SAW sensor device 100. Because the valves 321, 322, 323 and 324 control the inflow/outflow of the liquid, the valves 321, 322, 323 and 324 are connected to at least the first sample chamber 211 and the second sample chamber 212, each containing sample solutions. Additionally, the valves 321, 322, 323 and 324 may be connected to the first sample chamber 211 and the second sample chamber 212, as well as the first disposal chamber 220, as will be described in greater detail below.

The negative pressure pump 330 and/or the positive pressure pump 335 controls the flow of the liquid through the main body 200 including the SAW sensor 400 disposed therein. Specifically, the samples in the first sample chamber 211 and the second sample chamber 212 move to the first disposal chamber 220 through the SAW sensor 400 by a network of channels based on a pressure difference from the negative pressure pump 330 and/or the positive pressure pump 335 (hereinafter collectively referred to as "pumps"). More specifically, the pumps compress and/or decompress the first sample chamber 211, the second sample chamber 212 and/or the first disposal chamber 220 (hereinafter collectively referred to as "chambers"), thereby providing a driving force to transfer the liquid samples from the first sample chamber 211 and the second sample chamber 212 to the first disposal chamber 220 through the SAW sensor 400.

The pumps compress or decompress the chambers using positive and/or negative pressures. Therefore, the positive pressure pump 335 is disposed proximate to and in fluid communication with the first sample chamber 211 and the second sample chamber 212, which have the liquid flowing to the SAW sensor 400. In contrast, the negative pressure pump 330 is disposed proximate to and in fluid communication with the first disposal chamber 220, which receives the liquid expelled from the SAW sensor 400, as shown in FIG. 1.

Therefore, in an exemplary embodiment, the pump is the negative pressure pump 330, which is disposed at an outflow portion of the SAW sensor device 100, e.g., at an outlet of the liquid controller 310, as shown in FIG. 1. Thus, when the valve 323, connected to the first disposal chamber 220, is connected to the negative pressure pump 330, pressure is sequentially applied to the first disposal chamber 220, the SAW sensor 400, the first sample chamber 211 and the second sample chamber 212. As a result, when air pressure in the first disposal chamber 220 is reduced by ventilating the first sample chamber 211 and the second sample chamber 212 using the negative pressure pump 330, the liquid in the first sample chamber 211 and the second sample chamber 212 move sequentially to the SAW sensor 400 and then to the first disposal chamber 220, due to a negative pressure, e.g., a vacuum (relative to pressures in the first sample chamber 211 and the second sample chamber 212), created in the disposal chamber 220 by the negative pressure pump 330.

In an alternative exemplary embodiment, the positive pressure pump 335 may be disposed at an inflow portion of the device, e.g., an inlet of the liquid controller 310, as also shown in FIG. 1. Accordingly, when the valves 321 and 322, connected to the first sample chamber 211 and the second sample chamber 212, respectively, are connected to the positive pressure pump 335, the first disposal chamber 220 is ventilated, and air is thereby exhausted from the positive pressure pump 335 and flows into the first sample chamber 211 and the second sample chamber 212 through the valves 321 and 322, respectively. As a result, the liquid moves to the SAW sensor 400 along channels (described in greater detail below) due to a positive pressure (relative to a pressure in the SAW sensor and first disposal chamber 220) generated in the first sample chamber 211 and the second sample chamber 212 by the positive pressure pump 335.

It will be noted that, in alternative exemplary embodiments, either or both the negative pressure pump 330 and the positive pressure pump 335 are included in the SAW sensor device 100.

In an exemplary embodiment, the liquid controller 310 may be directly or, alternatively, indirectly connected to the main body 200 to control the flow of the sample therethrough. For example, as best shown in FIGS. 2(a) and 2(b), the valves 321 and 322 are connected to the first sample chamber 211 and the second sample chamber 212, respectively, while the valves 323 and 324 are connected to the first disposal chamber 220 and the second disposal chamber 230, respectively. In addition, the valves 323 and 321 may be connected to the negative pressure pump 330 (FIG. 1) and the positive pressure pump 335 (FIG. 1), respectively. Thus, the liquid controller 310 according to an exemplary embodiment includes a structure in which the negative pressure pump 330, the valve 323 and the first disposal chamber 220 are be sequentially connected, but alternative exemplary embodiments are not limited thereto.

In an exemplary embodiment, to connect the valves 321, 322, 323 and 324 (hereinafter collectively referred to as "valves") and/or the pumps to the chambers, openings 250, e.g. apertures 250, may be formed in a surface of the first sample chamber 211 and the second sample chamber 212, as well as in a surface of the first disposal chamber 220 and the second disposal chamber 230. Accordingly, the first sample chamber 211 and the second sample chamber 212, as well as the first disposal chamber 220 and the second disposal chamber 230, may be connected to the valves and/or the pumps by channels at corresponding respective portions through the openings 250.

In an exemplary embodiment, for example, the valves may be connected substantially perpendicular to the surfaces of the first sample chamber 211 and the second sample chamber 212 and/or the first disposal chamber 220 via the openings 250. As a result, a distance and time required to apply the pressure to the chambers is effectively minimized.

As discussed above, the first sample chamber 211, the second sample chamber 212, the first disposal chamber 220 and the second disposal chamber 230 may each include at least one of the openings 250 to allow the liquid to flow into or out of the each of the chambers. In addition to the openings 250, the first sample chamber 211 and the second sample chamber 212 may also include additional openings 260, e.g., additional apertures 260, for connection to the SAW sensor 400 and/or to other chambers, as shown in FIGS. 2(a) and 2(b). The channels may be coupled to the openings 250 and/or the additional openings 260, thereby forming a liquid path through the main body 200.

More specifically, referring to FIGS. 1-3, the openings 250, hereinafter referred to as "first openings 250," are formed in the first sample chamber 211, the second sample chamber 212, the first disposal chamber 220 and the second disposal chamber 230, while second openings 350 (e.g., second apertures 350), positions of which correspond to the first openings 250 of the main body 200, are formed in the cover 300 disposed above the main body 200, as best shown in FIGS. 2(a) and 2(b). In addition, the second openings 350 are connected to the valves 321, 322, 323 and 324, as shown in FIG. 2(a). However, it will be noted that alternative exemplary embodiments are not limited to the configuration or components shown in FIGS. 2(a) and 2(b).

As shown in FIG. 1, a sealing member 360, such as an O-ring, may be disposed at the second opening 350 connecting the cover, including the liquid controller 310 therein/thereon, to the main body 200, to substantially increase reliability of control of the sample liquid and to effectively prevent contact between the sample liquid and the liquid controller 310.

The liquid controller 310 may be disposed separate from the main body 200 and independently disposed on the main body 200, or, alternatively, may be integrated with the main body 200.

The liquid controller 310 may also include a baffle (not shown), such as a plug, obstacle or other device, which changes the liquid flow through the liquid controller 310.

Thus, the SAW sensor device according to an exemplary embodiment includes the first sample chamber 211, the second sample chamber 212 and the first disposal chamber 220. The first sample chamber 211 and the second sample chamber 212 contain a portion of the sample liquid that does not pass through the SAW sensor 400, and the first disposal chamber 220 contains a portion of the sample liquid that passes through the SAW sensor 400.

In alternative exemplary embodiments, multiple sample chambers may be provided, and each may contain a different sample from the other sample chambers. The samples may be liquids, and examples of the liquids include, but are not limited to, a solution containing a target material (hereinafter, referred to as a "target sample"), a secondary reaction solution, a reference solution and a washing solution. One or more target samples may be used.

Examples of the target samples may include, but are not limited to, biological samples, such as saliva, sputum, cerebrospinal fluid, blood, serum, plasma, urine and biopsy materials.

The target sample is a solution including a target material. The target material is a material to be detected by the SAW sensor 400.

Examples of the target materials may include, but are not limited to, bio molecules such as proteins, antibodies, antigens, deoxyribonucleic acid ("DNA"), ribonucleic acid ("RNA"), viral cells, bacterial cells, animal cells and tissues, and bio products such as toxins generated therefrom.

The reference solution is a liquid compared to the target sample for comparison by signal analysis. The reference solution may have similar characteristics, such as viscosity, conductivity and density, to the target sample, and may be a buffer solution.

The reference solution may be the same as the washing solution.

Referring again to FIG. 1, side surfaces 240 of the first sample chamber 211, the second sample chamber 212 and/or the first disposal chamber 220 may be tapered at a slope with respect to an imaginary plane substantially perpendicular to a plane defined by the upper surface of the main body 200 (e.g., may be tapered at an acute angle from the y-axis shown in FIG. 3). Because of the slope, a moving distance of the liquid is reduced, and an acceleration force is provided during the moving of the liquid. As a result, unnecessary loss of the liquid is thereby reduced.

In an exemplary embodiment, the acute angle of the slope may be, but is not limited to, from about 1 degree (°) to about 60° or, alternatively, may be from about 5° to about 30°.

As discussed above, in the SAW sensor device according to an exemplary embodiment, the chambers and the SAW sensor 400 are in fluid communication with each other through the channels.

More specifically, as shown in FIGS. 1-3, the channels include the first channels 510, connecting the first sample chamber 211 and the second sample chamber 212 to the SAW sensor 400, and the second channel 520 connecting the SAW sensor 400 to the first disposal chamber 220. It will be noted that alternative exemplary embodiments are not limited to the foregoing components, and may further include additional channels connecting additional chambers and/or components of the SAW sensor device 100.

The first channels 510 and the second channels 520 disposed in the main body 200 to form liquid paths therein. However, the first channels 510 and the second channels 520 prevent the liquids from moving when external power is not applied to the SAW sensor device 100 or the SAW sensor device 100 is not in operation.

In an exemplary embodiment, the first channels 510, connecting the first sample chamber 211 and the second sample chamber 212 to the SAW sensor 400, allow the liquid to flow upward from lower portions of the first sample chamber 211 and the second sample chamber 212 to an upper, e.g., top, surface of the SAW sensor 400 (as viewed in FIGS. 1 and 3). Accordingly, the liquid in the first sample chamber 211 and the second sample chamber 212 are effectively prevented from moving through the channels without external power, thereby easily controlling the flow of the liquid during operation, while preventing the liquids from moving when external power is not applied to the SAW sensor device 100 or the SAW sensor device 100 is not in operation.

As shown in FIG. 1, the first channel 510 extends upward (e.g., along the y-axis, as shown in FIG. 3) toward the upper surface of the main body 200, e.g., towards the cover 300 and liquid controller 310, from the lower portion of the first sample chamber 211 and the second sample chamber 212 (note that only the first the first sample chamber 211 is visible in the cross-section shown in FIG. 1). Thereafter, the first channel 510 extends substantially perpendicular to a plane defined by a lower surface of the first sample chamber 211 and the second sample chamber 212 toward the SAW sensor 400 (e.g., along the x-axis of FIG. 3), and then extends downward and substantially perpendicular to the upper surface of the SAW sensor 400.

In an exemplary embodiment, the second channel 520, connecting the SAW sensor 400 to the first disposal chamber 220, allows the liquid to flow upward from and substantially perpendicular to the plane defined by the upper surface of the SAW sensor 400, and then to flow into the first disposal chamber 220. Thus, the liquid moving to the first disposal chamber 220 is effectively prevented from flowing backward to the SAW sensor 400.

As shown in FIG. 1, the second channel 520 extends upward from and substantially perpendicular to the plane defined by the upper surface of the SAW sensor 400 (e.g., along the y-axis of FIG. 3), and is connected to an upper portion of the first disposal chamber 220, e.g., at a side of the first disposal chamber 220 facing the SAW sensor 400. Alternatively, the second channel 520 may extend upward from and substantially perpendicular to the plane defined by the upper surface of the SAW sensor 400, and then be connected to a lower portion of the first disposal chamber 220 at the side thereof facing the SAW sensor 400. Thus, in an exemplary embodiment, the backward flow of the sample liquid in the first disposal chamber 220 is effectively prevented from flowing backward into the SAW sensor 400.

It will be noted that, in alternative exemplary embodiment, the structures and/or arrangements of the first channels 510 and the second channels 520 are not limited to the foregoing description, and any structure connecting the chamber to the SAW sensor 400 is included in the scope of the general inventive concept disclosed herein.

In an exemplary embodiment, external channels, configured to connect to an external device, may also be included in the SAW sensor device 100. More specifically, first external channels 540 and second external channels 550 may be provided, as shown in FIGS. 1-3. Moreover, the first external channels 540 and second external channels 550, as well as the openings 250, may be disposed higher along the y-axis than the top surfaces of the chambers, as also shown in FIGS. 1-3. Accordingly, the external pressure provided by the pumps, e.g., the transfer driving force of the liquid, may be applied to at a lower portion of the chambers from an upper portion thereof. Additionally, the first external channels 540 and the second external channels 550 and/or the openings 250 may be engaged with the valves, as discussed above, and may thus control opening and closing of the chambers for ventilation when the external pressure is introduced by the pumps.

In an exemplary embodiment, a number of the sample chambers and/or the disposal chambers may be more than one. For example, an alternative exemplary embodiment may include two or three of each of the sample chambers and the disposal chambers. In addition, an alternative exemplary embodiment may also include more than one SAW sensor 400. In these alternative exemplary embodiments, however, it will be noted that connections between the chambers and/or or between the chambers and the SAW sensors is not limited to the foregoing discussion, as long as the abovementioned components can be ventilated as described herein.

As discussed above, the SAW sensor 400 detects characteristics of a target material, but specific configurations of the SAW sensor 400 are not particularly limited. In general, the SAW sensor 400 according to an exemplary embodiment includes a pair of inter-digital transducers ("IDTs"), e.g., metal electrodes (not shown), disposed on a substrate 410 (FIG. 1) having a piezoelectric characteristic.

More specifically, the piezoelectric material forming the substrate 410 is a material having electrical characteristics which are converted, e.g., are altered, when a mechanical signal is applied thereto (e.g., having a "Piezoelectric effect"), or, alternatively, generating a mechanical signal when an electrical signal is applied thereto (e.g., a "reverse" Piezoelectric effect). In an exemplary embodiment, for example, the piezoelectric material may include lithium niobate ($LiNbO_3$), lithium tantalite ($LiTaO_3$), lithium teraborate ($Li_2B_4O_7$), barium titanate ($BaTiO_3$), lead zirconate ($PbZrO_3$), lead titanate ($PbTiO_3$), Zr-doped lead titanates ($PbZr_xTi_{1-x}O_3$ or "PZT"), zinc oxide (ZnO), gallium arsenide (GaAs), quartz or niobate, but alternative exemplary embodiments are not limited thereto.

The IDTs (not shown) are an interface between an electrical circuit and an acoustic delay line (not shown), which may include, but is not limited to, a thin metal film of an aluminum alloy, a copper alloy or gold.

A first IDT of the pair of IDTs generates a surface acoustic wave based on a signal applied thereto. Accordingly, the first IDT is referred to as an "input IDT" or a "transmitter." The surface acoustic wave generated by the first IDT is delivered to a second IDT of the pair of IDTs by expansion and compression with a specific frequency along a surface of the substrate, and is converted into an electrical signal due to the reverse piezoelectric effect in the second. The second IDT is referred to as an "output IDT" or a "receiver."

A receptor 405 (FIG. 2), which binds to a target material present in a target sample, is disposed on a surface of the SAW sensor 400. The receptor may be, but is not particularly limited to, a material that specifically reacts with the target material.

In an exemplary embodiment, for example, the receptor may include proteins, antigens, antibodies, enzymes, DNA, RNA, peptide nucleic acids ("PNA," e.g., artificial DNA), cells or olfactories.

The SAW sensor device 400 may include a plurality of the SAW sensors 400, depending on a type or kind of liquids, target materials and receptors to be analyzed. In addition, the SAW sensor device 100 may include an oscillator 600 (FIG. 1), which generates a signal configured to induce a SAW, but alternative exemplary embodiments are not limited thereto.

A method of controlling a sample liquid flow in an exemplary embodiment of the SAW sensor device 100 will now be described in further detail. It will be noted that, while an exemplary embodiment including the negative pressure pump 330 will now be described, that alternative exemplary embodiments are not limited thereto, but may instead include either or both the negative pressure pump 330 and/or the positive pressure pump, as discussed in greater detail above. Referring to FIGS. 1-3, when the valve 323 is gated, e.g., is opened, and then the negative pressure pump 330 is driven, a negative air pressure, e.g., a vacuum, is formed in the chambers by outflow of air. Accordingly, a pressure gradient is generated between the air and the liquid in the chambers, causing the liquid to move. Specifically, the liquid moves from the first sample chamber 211 and the second sample chamber 212 to an inlet port of the SAW sensor 400 through the first channel 510 by gating the valve 323 connected to the negative pressure pump 330. As a result, the liquid flows through the SAW sensor 400, and moves to the first disposal chamber 220 through an outlet port of the SAW sensor 400.

Additionally, when the valve 321 of a desired chamber, e.g., the first sample chamber 211, is gated, the pressure gradient between the air and liquid in the chambers is removed, by the liquid flowing out of the chamber. In contrast, when the valve 321 (and, subsequently, the openings 250 and 350) are closed, the pressure gradient is not able to be offset, and the liquid does not flow through the chamber.

Accordingly, in an exemplary embodiment, the liquid flow to desired portions of the SAW sensor 400 is controlled, even though the liquid controller 310, e.g., the valves 321, 322, 323 and 324, is not disposed internally within the main body 200 of the SAW sensor device 100. As a result, analysis errors caused by contamination of the target sample are substantially reduced and/or are effectively minimized. In addition, the liquid controller 310, including the valves 321, 322, 323 and 324 and the negative pressure pump 330, for example, are re-usable and may therefore be used for repeated analyses, thereby substantially reducing costs.

When the liquid flow is controlled by the inflow/outflow of the air, and, more particularly, when the sample liquids flow into the SAW sensor 400, air bubbles generated by the air may cause noise, resulting in an undesired change in a signal outputted from the SAW sensor 400. Specifically, when a first liquid is injected into the first sample chamber 211 and is thereafter replaced with a second liquid, noise may be generated due to air bubbles formed during injection of the first liquid, so that a reliability and/or accuracy of sensing of the second liquid is adversely affected.

To prevent this, the SAW sensor device 100 according to an exemplary embodiment may further include an additional chamber configured to capture the air bubbles, thereby effectively preventing the noise.

For example, referring again to FIGS. 1-3, to prevent inflow of the air bubbles to the SAW sensor, a second disposal chamber 230 captures the air bubbles. The second disposal chamber 230 may be connected between the first sample chamber 211, the second sample chamber 212 and the SAW sensor 400 via a third channel 530.

Accordingly, after a first liquid moves from the first sample chamber 211 to the SAW sensor 400 via the first channel 510, air bubbles contained in the first channel 510 are captured by the second disposal chamber 230 via the third channel 530, and a second liquid may thereafter move to the SAW sensor 400, such as from the second sample chamber 212 via the first channel 510, for example.

Referring to FIGS. 1-3, an operating sequence of an exemplary embodiment of the SAW sensor device 100 including the negative pressure pump 330 connected to the valve 323 disposed above the first disposal chamber 220 will now be described in further detail.

The valve 323 disposed above the first disposal chamber 220 is gated, e.g., is opened, to form a vacuum in the first disposal chamber 220 and the first sample chamber 211, thereby increasing a pressure in the first liquid in the first sample chamber 211, resulting in the first liquid flowing into the SAW sensor 400.

The valve 324 above the second disposal chamber 230 is gated to increase pressure in the second liquid in the second sample chamber 212, resulting in capturing the remaining solution of the first sample and air bubbles in the first channel 510 in the second disposal chamber 230 via the third channel 530.

The valve 323 above the first disposal chamber 220 is gated again to increase pressure in the second liquid in the second sample chamber 212, resulting in injecting the second liquid into the SAW sensor 400.

In an alternative exemplary embodiment, a system for analyzing a target material in a sample is also provided. More specifically, the system includes: a first SAW sensor device 100 (hereinafter referred to as a "test SAW sensor device") in which a receptor 405 (FIG. 2) which reacts with a target material is disposed on a surface of a SAW sensor 400 of the test SAW sensor device; and a second SAW sensor device 100 (hereinafter referred to as a "control SAW sensor device"). In an exemplary embodiment, a SAW sensor 400 of the control SAW sensor device does not include a receptor disposed a surface thereof.

In an exemplary embodiment of the system, a presence and quantity of the target samples is analyzed based on a difference between a signal generated from the binding of the target material to the receptor on the sensor surface of the test SAW sensor device and a signal generated from the control SAW sensor device not having the receptor.

In yet another alternative exemplary embodiment, a method of controlling a liquid using the SAW sensor device 100 is also provided. Specifically, the method of controlling the liquid includes allowing a liquid in the first sample chamber 211 and/or the second sample chamber 212 to horizontally move (e.g., to move along the x- and/or z-axes of FIG. 3) and to the SAW sensor 400 by a transfer driving force provided from the liquid controller 310 disposed outside, e.g., external to, the main body 200 of the SAW sensor device 100.

The transfer driving force may be atmospheric pressure, e.g., air pressure. In an exemplary embodiment, the liquid controller 310 is not in direct contact with the liquid in the main body 200, since it is disposed outside the main body 200, and instead allows the air to move into and out of the main body 200 to drive the liquid therein. Thus, contamination of the liquid controller 310 by the liquid is substantially reduced and/or is effectively prevented.

Sensing using the SAW sensor device 100 according to exemplary embodiments may further include stabilizing a signal by installing the SAW sensor device 400 proximate to the oscillator 600 and operating the oscillator 600, setting an oscillation signal to a base line by injecting a reference solution into the first sample chamber 211 and/or the second sample chamber 212 and thereafter into the SAW sensor 400, and monitoring the oscillation signal while injecting the target sample in the first sample chamber 211 and/or the second sample chamber 212 into the SAW sensor 400.

The monitored signal may be a frequency, a phase or an amplitude, for example, but alternative exemplary embodiments are not limited thereto. When the target sample moves to the SAW sensor 400 from the first sample chamber 211 and/or the second sample chamber 212, the receptor 405 attached to the upper surface of the SAW sensor 400 reacts with a target material in the target sample, resulting in a wave change in the monitored signal. Thus, the presence, content and type of the target material in the target sample are detected based on a difference between a base line and the wave change when a target sample has been injected.

The liquid passing through the SAW sensor 400 then moves to the first disposal chamber 220 to be disposed.

In an exemplary embodiment, the method may further include removing air bubbles remaining in a channel, such that the air bubbles are not injected into the SAW sensor 400 after the liquid moves therethrough. After sensing, the SAW sensor device is washed with a washing solution, and the base signal may be re-measured.

Thus, in a SAW sensor device according to exemplary embodiments, a liquid controller is not disposed in a main body through which a liquid flows, and the liquid is therefore not in contact with the liquid controller. Thus, noise due to contamination of the liquid controller, such as contamination of a valve or a pump thereof, for example, is substantially reduced and/or is effectively minimized. In addition, reuse of the liquid controller is possible, and the SAW sensor device according to an exemplary embodiment therefore provides substantially improved economical and industrial efficiencies.

While exemplary embodiments have been disclosed herein, it will be understood that additional alternative exemplary embodiments may be possible. Such additional alternative exemplary embodiments are not to be regarded as a departure from the spirit or scope of the general inventive concept disclosed herein. Rather, the exemplary embodiments described herein are provided so that this disclosure will be thorough and complete and will fully convey the general inventive concept to those skilled in the art.

Thus, it will be understood by those of ordinary skill in the art that various changes in form and details may be made in the exemplary embodiments described herein without departing from the spirit or scope of the present invention as defined by the following claims.

What is claimed is:

1. A surface acoustic wave sensor device comprising:
   a main body comprising:
      a sample chamber;
      a surface acoustic wave sensor connected to the sample chamber;
      a first disposal chamber connected to the surface acoustic wave sensor; and
      channels connecting the sample chamber, the surface acoustic wave sensor and the first disposal chamber; and
   a liquid controller disposed external to the main body,
   wherein the liquid controller controls flow of a sample through the main body.

2. The surface acoustic wave sensor device of claim 1, wherein the liquid controller is disposed above the main body.

3. The surface acoustic wave sensor device of claim 1, further comprising a cover disposed on an upper surface of the main body, wherein
   the upper surface of the main body is disposed opposite a lower surface of the main body, the lower surface disposed closer to an oscillator than the upper surface, and
   the liquid controller is disposed on the cover.

4. The surface acoustic wave sensor device of claim 1, wherein the liquid controller controls the flow of the sample by adjusting at least one of inflow of air to the main body and outflow of air from the main body.

5. The surface acoustic wave sensor device of claim 1, wherein the liquid controller comprises one or more of valves and a pump.

6. The surface acoustic wave sensor device of claim 5, wherein the valves are connected to at least one of the sample chamber and the first disposal chamber.

7. The surface acoustic wave sensor device of claim 5, wherein the pump comprises one of a positive pressure pump and a negative pressure pump.

8. The surface acoustic wave sensor device of claim 5, wherein
   when the pump is the positive pressure pump, the pump is disposed at an inlet of the liquid controller, and
   when the pump is the negative pressure pump, the pump is disposed at an outlet of the liquid controller.

9. The surface acoustic wave sensor device of claim 1, wherein
   the sample chamber and the first disposal chamber include openings formed in surfaces thereof, and
   the liquid controller is in fluid communication with the main body via the openings.

10. The surface acoustic wave sensor device of claim 3, wherein a side of at least one of the sample chamber and the first disposal chamber is inclined at an acute angle with respect to an imaginary plane aligned substantially perpendicular to a plane defined by the upper surface of the main body.

11. The surface acoustic wave sensor device of claim 10, wherein the acute angle is from about 1 degree to about 60 degrees.

12. The surface acoustic wave sensor device of claim 10, wherein the acute angle is from about 5 degrees to about 30 degrees.

13. The surface acoustic wave sensor device of claim 1, wherein the sample is a liquid which includes one selected from a group consisting of a solution containing a target material, a reference solution, a washing solution, a buffer solution and any combinations thereof.

14. The surface acoustic wave sensor device of claim 3, wherein
   the channels comprise a first channel connecting the sample chamber to the surface acoustic wave sensor, and
   the sample flows through the first channel upward toward the upper surface of the main body from a lower portion of the sample chamber, and thereafter downward toward an upper surface of the surface acoustic wave sensor.

15. The surface acoustic wave sensor device of claim 14, wherein the first channel extends upward away from the lower portion of the sample chamber toward the upper surface of the main body and substantially perpendicular to a side of the sample chamber facing the surface acoustic wave sensor, and thereafter extends downward away from the upper surface of the main body toward the upper surface of the surface acoustic wave sensor substantially perpendicular to a plane defined by the upper surface of the surface acoustic wave sensor.

16. The surface acoustic wave sensor device of claim 14, wherein
   the channels further comprise a second channel connecting the surface acoustic wave sensor to the first disposal chamber, and
   the sample flows through the second channel upward toward the upper surface of the main body from the upper surface of the surface acoustic wave sensor, and thereafter into the first disposal chamber.

17. The surface acoustic wave sensor device of claim 14, wherein the second channel extends upward away from the upper surface of the surface acoustic wave sensor toward the upper surface of the main body and substantially perpendicular to a plane defined by the upper surface of the surface acoustic wave sensor, and thereafter extends substantially parallel to the plane defined by the upper surface of the surface acoustic wave sensor toward the first disposal chamber to connect thereto.

18. The surface acoustic wave sensor device of claim 1, further comprising a second disposal chamber connected between the sample chamber and the surface acoustic wave sensor.

19. The surface acoustic wave sensor device of claim 18, wherein the second disposal chamber includes an opening formed therein and through which the liquid controller is fluidly connected to the main body.

20. A surface acoustic wave sensor system comprising:
   a first surface acoustic wave sensor device; and
   a second surface acoustic wave sensor device, wherein
   each of the first surface acoustic wave sensor device and the second surface acoustic wave sensor device comprises:
      a main body comprising:

a sample chamber;

a surface acoustic wave sensor connected to the sample chamber;

a first disposal chamber connected to the surface acoustic wave sensor; and channels connecting the sample chamber, the surface acoustic wave sensor and the first disposal chamber; and a liquid controller disposed external to the main body, wherein the liquid controller controls flow of a sample through the main body, a receptor is disposed on a surface of the surface acoustic wave sensor of the first surface acoustic wave sensor device, and a receptor is not disposed on a surface of the surface acoustic wave sensor of the second surface acoustic wave sensor device.

* * * * *